(12) United States Patent
Seedhom et al.

(10) Patent No.: US 7,427,284 B2
(45) Date of Patent: Sep. 23, 2008

(54) FIXATION TECHNOLOGY

(75) Inventors: Bahaa Seedhom, Summerbridge (GB); Takashi Toyoda, Tokyo (JP); Michael Pullan, Leeds (GB)

(73) Assignee: University of Leeds, Leeds (GB)

( * ) Notice: Subject to any disclaimer, the term of this patent is extended or adjusted under 35 U.S.C. 154(b) by 672 days.

(21) Appl. No.: 10/148,503

(22) PCT Filed: Dec. 4, 2000

(86) PCT No.: PCT/GB00/04624

§ 371 (c)(1),
(2), (4) Date: Sep. 18, 2002

(87) PCT Pub. No.: WO01/39694

PCT Pub. Date: Jun. 7, 2001

(65) Prior Publication Data

US 2003/0135209 A1    Jul. 17, 2003

(30) Foreign Application Priority Data

Dec. 3, 1999 (GB) .................. 9928569.4
Jun. 27, 2000 (GB) .................. 0015640.6
Nov. 9, 2000 (GB) .................. 0027394.6

(51) Int. Cl.
  *A61B 17/00* (2006.01)
(52) U.S. Cl. .................. 606/79; 606/151

(58) Field of Classification Search .................. 606/73, 606/79, 83, 82, 80, 300, 322, 151; 623/17.11–16, 623/11.11, 16.11, 23.72, 23.75; 424/423, 424/484
See application file for complete search history.

(56) References Cited

U.S. PATENT DOCUMENTS 3,030,951 A  *  4/1962  Mandarino .................. 606/60

(Continued)

FOREIGN PATENT DOCUMENTS

DE         43 17 448         11/1994

(Continued)

*Primary Examiner*—Eduardo C. Robert
*Assistant Examiner*—David Comstock
(74) *Attorney, Agent, or Firm*—Kirton & McConkie; Evan R. Witt

(57) ABSTRACT

Provided herein is a method for the repair of damaged tissue present at or on the surface of bone in an animal, the method comprising forming a narrow groove around at least part of said damaged tissue, which groove extends into the bone below the damaged tissue, replacing the tissue around which the groove extends by at least one layer of biocompatible replacement material, and anchoring the material to the bone using a retainer extending from the material into the groove; instruments for use in the repair of damaged tissue and kits comprising said instruments.

24 Claims, 9 Drawing Sheets

U.S. PATENT DOCUMENTS

| | | | |
|---|---|---|---|
| 4,059,115 A * | 11/1977 | Jumashev et al. | 606/82 |
| 4,458,678 A * | 7/1984 | Yannas et al. | 602/48 |
| 4,649,918 A | 3/1987 | Pegg et al. | |
| 4,839,215 A * | 6/1989 | Starling et al. | 428/131 |
| 5,049,150 A * | 9/1991 | Cozad | 606/80 |
| 5,067,964 A | 11/1991 | Richmond et al. | |
| 5,366,508 A * | 11/1994 | Brekke | 623/23.58 |
| 5,535,756 A | 7/1996 | Parasher | |
| 5,540,691 A * | 7/1996 | Elstrom et al. | 606/64 |
| 5,571,189 A * | 11/1996 | Kuslich | 623/17.12 |
| 5,591,187 A * | 1/1997 | Dekel | 606/180 |
| 5,741,257 A * | 4/1998 | Kirsch | 606/69 |
| 5,782,835 A | 7/1998 | Hart et al. | |
| 5,827,289 A * | 10/1998 | Reiley et al. | 606/86 |
| 5,919,234 A * | 7/1999 | Lemperle et al. | 623/23.72 |
| 5,928,238 A * | 7/1999 | Scarborough et al. | 606/79 |
| 5,964,805 A | 10/1999 | Stone | |
| 5,989,269 A * | 11/1999 | Vibe-Hansen et al. | 606/151 |
| 6,007,496 A * | 12/1999 | Brannon | 600/565 |
| 6,019,764 A * | 2/2000 | Bartee | 606/86 |
| 6,071,284 A * | 6/2000 | Fox | 606/80 |
| 6,077,989 A * | 6/2000 | Kandel et al. | 623/13.17 |
| 6,080,176 A | 6/2000 | Young | |
| 6,080,194 A * | 6/2000 | Pachence et al. | 623/23.76 |
| 6,089,867 A * | 7/2000 | Filho | 433/215 |
| 6,093,200 A * | 7/2000 | Liu et al. | 606/228 |
| 6,132,214 A * | 10/2000 | Suhonen et al. | 433/201.1 |
| 6,146,420 A * | 11/2000 | McKay | 623/17.16 |
| 6,179,840 B1 * | 1/2001 | Bowman | 606/72 |
| 6,258,044 B1 * | 7/2001 | Lonky et al. | 600/569 |
| RE37,479 E * | 12/2001 | Kuslich | 623/17.11 |
| 6,352,558 B1 * | 3/2002 | Spector | 623/18.11 |
| 6,391,034 B1 * | 5/2002 | Adamson et al. | 606/131 |
| 6,425,923 B1 * | 7/2002 | Stalcup et al. | 623/23.58 |
| 6,533,821 B1 * | 3/2003 | Lally | 623/23.62 |
| 6,712,822 B2 * | 3/2004 | Re et al. | |
| 7,004,974 B1 * | 2/2006 | Larsson et al. | 623/23.56 |
| 7,141,072 B2 * | 11/2006 | Geistlich et al. | 623/23.74 |
| 2001/0039455 A1 * | 11/2001 | Simon et al. | 623/23.51 |
| 2001/0049527 A1 * | 12/2001 | Cragg | 606/61 |
| 2002/0173855 A1 * | 11/2002 | Mansmann | 623/23.72 |
| 2003/0036801 A1 * | 2/2003 | Schwartz et al. | 623/23.63 |

FOREIGN PATENT DOCUMENTS

| | | |
|---|---|---|
| DE | 195 03 504 | 3/1996 |
| DE | 198 03 673 | 8/1999 |
| EP | 0 228 752 | 7/1987 |
| EP | 0 505 634 | 9/1992 |
| GB | 638892 | 6/1950 |
| WO | WO 93/07819 | 4/1993 |
| WO | WO 94/09722 | 5/1994 |
| WO | WO 96/24302 | 8/1996 |
| WO | WO 96/24304 | 8/1996 |
| WO | WO 97/46665 | 12/1997 |
| WO | WO 98/08469 | 3/1998 |
| WO | WO 98/34569 | 8/1998 |

* cited by examiner

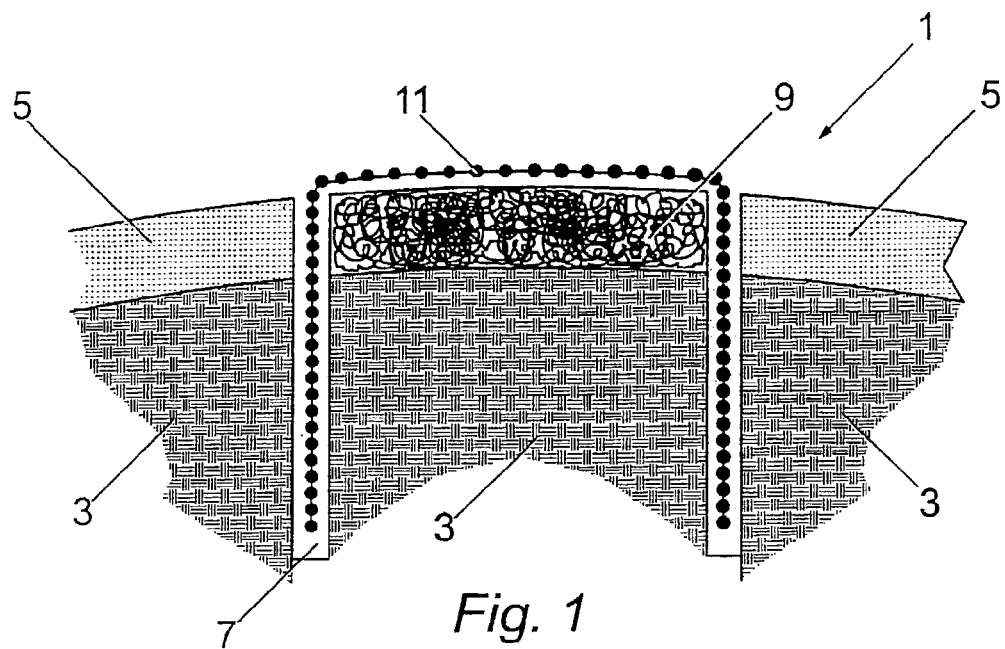
Fig. 1
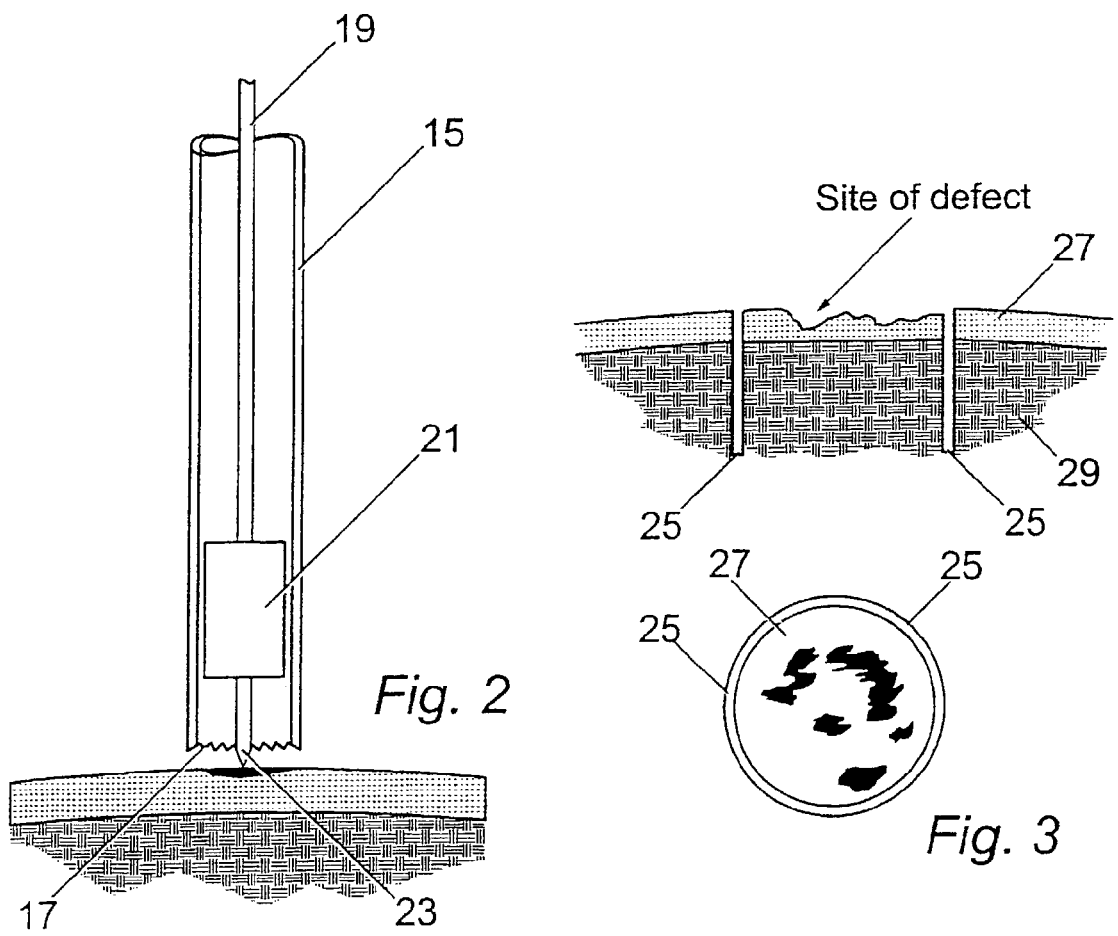
Fig. 2
Fig. 3

FIXATION TECHNOLOGY

CROSS REFERENCE TO RELATED APPLICATIONS

This is a U.S. National Stage application of International Application No. PCT/GB00/04624, filed Dec. 4, 2000, which was published in English under PCT Article 21(2), which in turn claims the benefit of Great Britain Application Nos. 0027394.6, filed Nov. 9, 2000; 0015640.6, filed Jun. 27, 2000; and 9928569.4, filed Dec. 3, 1999.

FIELD OF THE INVENTION

This invention relates to methods instruments and devices involved in the repair of damaged tissue present at or on the surface of bone, and/or for filling cavities at the surface of, or in the bones (eg condyles of a knee joint), in an animal, including a human being.

Reference will be made hereinbelow to the repair of damaged cartilage. It should be understood that the damaged tissue may be other types of tissue (eg bone, skin) including damaged surface of, or defects in, bone itself. Reference will also be made hereinbelow to the repair of cartilage of knee joints and again it should be understood that the present invention may be applied to other body joints and indeed to other organs of the body which consist of or incorporate bone or skin.

BACKGROUND OF THE INVENTION

Defects in the articular surfaces of the knee joint, especially in young active individuals, are currently a focus of interest by orthopaedic surgeons. Damage to cartilage which protects joints can result from either physical injure (eg osteochondral fracture, secondary damage due to cruciate ligament injury) or from disease (eg osteoarthritis, rheumatoid arthritis, aseptic necrosis, osteochondritis dissecans). Osteoarthritis results from general wear and tear of joints and is common in the elderly. Rheumatoid arthritis is an inflammatory condition which results in the destruction of cartilage. It is thought to be, at least in part., an autoimmune disease with suffers having a genetic predisposition to the disease. Orthopaedic prevention/repair of damaged joints is a significant burden on the medical profession both in terms of expense and time spent treating patients.

Drug intervention to ameliorate or prevent the onset of cartilage loss are available but do have significant disadvantages.

As an alternative to drug intervention, thus avoiding undesirable side effects, orthopaedic surgery is available in order to repair defects and prevent articular damage, thereby leading to serious degenerative changes in the joint. Such changes may result in the need for a total knee replacement which is particularly undesirable in young active individuals with a long life expectancy. If the lifetime of the implant is less than that of the patient, a revision procedure may be necessary. Preferably, such revision procedures are to be avoided, having regard to inconvenience to the patient. Furthermore implant revision procedures are both lengthy and very costly.

The use of surgical techniques to repair/replace damaged tissue in joints often requires the removal and donation of healthy tissue to replace the damaged or diseased tissue. There are three sources of donating tissue used in tissue engineering of this type:
i) autograft: tissue is removed from an area of the patient remote from the region to be repaired and grafted to the damaged region to effect the repair;
ii) allograft: tissue is removed from a donating individual, for example a cadaver, and transplanted to the damaged region; and
iii) xenograft: tissue is harvested from another animal species, for example a pig, and placed over the damaged area.

Autografts can be problematic due to the limited availability of suitable tissue and the added trauma to the patient during removal of the tissue from another part of the body to the damaged area. Allografts are limited by immunological reactivity of the host, availability of suitable donor tissue and the problem of transfer of infective agents. Xenografts are even more problematic due to the severe immunological reactivity.

Various techniques for cartilage repair are either in limited current use or under, development but publicly disclosed. The Osteochondral Autogenous Transplant System (OATS) of Arthrex Inc is arguably the most widely used method. Osteochondral plugs are harvested from a healthy donor and, more particularly, from a site which is claimed to be 'non-weight-bearing'. These plugs are transplanted into the site of the chondral defect. This procedure has been applied primarily in the knee joint.

However, there are no donor sites in the knee with cartilage of a comparable thickness to that of the deficient site which can be described as 'non-weight-bearing' areas. The sulcus terminalis, a frequently used site for harvesting such grafts, is in direct contact with the lateral meniscus at the position of full knee extension, and is therefore a weight-bearing site.

Furthermore, harvesting a large osteochondral plug from the sulcus terminalis may cause the lateral meniscus to become loose and thus impair its load-bearing function. As a result, all the tibio-femoral loads would be transmitted onto the small area of direct contact between the femur and tibia. The resultant stresses could be as high as those arising after meniscectomy with its consequential degenerative changes in the cartilage of the tibial plateau. Such changes have always been regarded as precursors to osteoarthritis.

While the OATS method provides a reasonable technique, including good instrumentation, for transplanting live autogenous grafts for repair of defects in cartilage, it involves introducing potentially damaging effects at other sites with the serious disadvantages discussed above. In addition, harvesting a plug from a donor site creates a new damage in the knee articular surface. For this reason, OATS would not be suitable for the repair of large defects. The use of OATS for small repairs would probably limit the magnitude of the problem discussed above, but it would also limit the indication for using this technique.

The technique known as Autogenous Chondrocyte Implants (ACI) of Genzyme Inc is a conceptually elegant approach which is gaining popularity, but still in limited use. The procedure is intended for repair of small as well as large irregular defects, and is achieved in a two stage surgery. In the first stage, chondrocytes (cartilage cells) are harvested from the patient and cultured in suspension. In the second stage of the operative procedure, cartilage residue is cleared from the repair site. The site is then covered with a piece of periosteal tissue which is sutured to the perimeter of the repair area. The chondrocytes are then injected into the repair site using a hypodermic syringe, puncturing the periosteum with the needle of the syringe. In a variation of this procedure, the periosteal tissue is applied to the repair site in the first stage of the operation to ensure that, by the time the chondrocytes are due to be injected, an adequate seal has formed between the tissue and the perimeter of the cartilage. There is a high probability of the chondrocytes escaping through the hole of the hypodermic needle in either version of the procedure.

A further problem with the second version of the procedure is the probability of tissue adhesions occurring between the periosteal tissue and the bottom of the repair site.

This procedure does not have an established rate of success and the quality of cartilage in the repair site is questionable. As with the OATS method, this procedure is not minimally invasive. Further, it is an extremely costly procedure It is also a disadvantage that it requires two operative procedures although the first stage is less invasive as it can be performed arthroscopically.

A procedure proposed by Smith & Nephew involves the production of cartilage discs formed by allogenic chondrocyte culture on an absorbable textile fabric. The discs are grown in the laboratory, the allogenic chondrocytes being cultured on a matrix of a non-woven mesh of a bioabsorbable material, typically polyglycolic acid. When this procedure is completed, the disc is supplied for implantation at the repair site.

An advantage of this method is that it does not involve damage to an intact healthy chondral site since the method uses allogenic sources. Furthermore the procedure is completed in a one stage operation.

The discs can be made in different sizes but there must be a limit to the size of the defect which can be repaired with a loose disc which is merely placed on the repair site. The implant could move freely in the joint. It could wrinkle under the influence of tangential forces and could be completely damaged as a result. This problem would be exacerbated by a low compressive modulus of the material.

A further disadvantage with this method is that the material, being an allograft, runs the risk of viral infection, for example, the HIV virus. Although a small risk, this is an inherent problem with any allograft.

A further problem to be anticipated with this type of graft is the compressive modulus of the material. It may be quite low and the material might be in need of mechanical conditioning (a time consuming and costly process) to achieve a modulus compatible with that of cartilage of the surrounding area.

The Depuy cartilage repair system is a disc of non-woven fabric made of bioabsorbable material that has a hard substrate which enables the implant to be attached to the bone. The shape of the disc allows repair of damaged areas of irregular shapes by using a plurality of discs in a close-packed array. The disadvantages with this system are that the use of too many adjacent hexagonal discs will result in much damage to the bone substrate, and, further the technique may require considerable skill and its application may also be time consuming.

STATEMENTS OF INVENTION

In its broadest aspect the invention relates to a method to repair damaged tissue by forming a groove in said damaged tissue which provides a foundation for the application of material to a site to be repaired wherein said material is anchored in place by securing means.

According to the present invention there is provided a method for the repair of damaged tissue present at or on the surface of bone in an animal, including a human being, the method comprising forming a narrow groove around said damaged tissue, which groove extends into the bone below the damaged tissue, replacing the tissue around which the groove extends by at least one layer of biocompatible replacement material, and anchoring the material to the bone by the use of retaining means extending from the material into the groove.

In a preferred method of the invention said repair extends to the replacement of damaged bone tissue in conjunction with the repair/replacement of tissue attached to bone, eg cartilage.

It is well known in the art that damage to joints can extend into bone tissue which requires remedial action to effect a complete repair. Materials used in the repair of bone are also well known in the art and include, by example and not by way of limitation, synthetic bone replacement material (eg hydoxyapatite blocks/granules, as well as hydroxyapatite filled polymers); pulverised bone; coral.

Preferably the groove is formed by a reaming device.

Preferably the depth of the groove is a multiple of the thickness of tissue which is replaced. For instance, where the tissue to be replaced is circular then the depth of the groove is preferably at least equal to the diameter of the tissue being replaced. It will be apparent to one skilled in the art that the groove is of sufficient depth to securely retain the replacement material so that it does not get dislodged as the joint articulates. The deeper the groove the more secure the implanted replacement material. However care must be taken to ensure the groove is not too deep since this would represent increased invasiveness.

Preferably the replacement material is in the form of at least one circular, crescent shaped or part circular pad(s) stacked on top of each other. More preferably still said replacement material comprises a plurality of pads. It will be apparent to one skilled in the art that the number of replacement pads used will be determined by the depth of the resultant recess formed after removal of damaged tissue.

It will also be apparent to one skilled in the art that replacement material is broadly construed as materials which facilitate repair such as, tissue (eg cartilage, bone, synovium), cells from different origins including chondrocytes, biocompatible gel, comprising tissue/cells, synthetic bone material, coral.

In conditions where extensive damage to tissue has occurred it is preferable to use at least two closely associated pads. For example, and not by way of limitation, FIG. 10 shows a pad arrangement wherein two concentric grooves are formed. A first pad is positioned within the first concentric groove at a site to be repaired. A second, larger concentric groove, is formed around the first concentric groove and a second, ring shaped pad, is positioned within the second concentric groove. In this arrangement, two retaining means are used to anchor the pads of replacement material at the site to be repaired.

The material may be bio-absorbable or non-bio-absorbable.

More preferably still said pad provides an increased surface area to which cells adhere and proliferate. More preferably still said pad promotes the differentiation of cells which adhere thereto.

Preferably said pad is adapted to provide a cell culture surface to which at least one of the following cell types adhere, proliferate and/or differentiate: chondrocytic progenitor cells (stem cells); chondrocytes or cartilage-forming cells. Furthermore cells can be genetically engineered to express gene products which, for example facilitate the attachment and/or differentiation of cells which infiltrate the pad.

Ideally said pad is immune silent. It will be apparent to one skilled in the art that it is desirable that the pad does not provoke an immune reaction in the patient.

Preferably the retaining means is in the form of a thin, flexible mesh, more preferably made of a woven fabric.

Alternatively, the retaining means is made of non-woven fabric.

More preferably said replacement material and said retaining means are, over at least part of their length, connected together.

In a further aspect of the present invention, there is provided a set of instruments for the repair of damaged tissue present at or on the surface of bone in an animal, including a human being, the set comprising means for forming a narrow groove around at least part of said damaged tissue, which groove extends into bone below the damaged tissue, means for removing damaged tissue around which the groove extends, and means for anchoring retaining means to the bone so as to retain replacement material at the site from which the damaged tissue has been removed.

Typically, the groove can be made with a, straight or curved punch or with an oscillating saw. It will be apparent to one skilled in the art that the use of an oscillating saw enables the surgeon to make geometric cuts around the damaged tissue thus minimising the damage to healthy tissue. For example, and not by way of limitation, the surgeon can make a series of angular cuts around a damaged area to surround the damaged tissue. Typically, this results in damaged tissue being sectioned by a polygonal series of cuts as depicted in FIG. 14.

Preferably, the means for forming the narrow groove is a reaming device.

Typically, the damaged tissue can be excised using a scraping device as depicted in FIGS. 4 and 5. Alternatively, or preferably, the damaged tissue is removed using a wire brush, FIG. 9. The use of a wire brush has advantages over the use of a scraping device. Firstly, the abrasive nature of a wire brush although effective at removing damaged cartilage does not have the propensity to damage the underlying bone, which does occur when using a scraping device. Secondly, the wire brush method of removal of tissue promotes tissue re-growth by slight damage to blood vessels in the underlying bone. This promotes local angiogenesis and tissue regrowth.

An alternative to the use of a wire brush to promote angiogenesis is shown in FIG. 16. Typically the device is a cylindrical rod at the end of which numerous needles are attached. The head including the needles is pressed against the subchondral plate to prick the bone plate at numerous sites and thereby result in a uniform distribution of angiogenesis over the repair site.

Preferably the wire brush is provided with guide means to restrict the abrasive action of the brush to the area of damaged tissue.

In situations where a scraping device is used to remove damaged cartilage, it is advantageous to use guard means to prevent the scraping device damaging surrounding healthy cartilage. Typically, a guard means is located in the groove to abut the scraping device during removal of the damaged cartilage. A guard means is manufactured from any robust, tensile materials to confer protection (eg steel, high density plastics).

A further alternative means to remove damaged tissue is a device which comprises a rotatable cutting head comprising a plurality of cutting edges, the cutting head being rotatable relative to a support member which supports the cutting head. An example of such an implement is illustrated in FIG. 17.

In the embodiment shown in FIG. 17, the instrument consists of a cutting head that is mounted on the end of a shank, the cutting action is achieved by rotating the shank while the head is moved over cartilage surface and while applying pressure onto the cutting head. The head has a substantially flat end with sharp edged grooves that are formed by making holes in the head in a perpendicular direction to the axis of rotation and by machining of an appropriate amount of material from the end. The end of the instrument being flat skids over the hard and relatively un-deformable surface of the underlying bone (without damaging it), when the instrument reaches the bony surface, after it has removed the cartilage layer.

Alternatively the cutting bead is attached directly to a handle which imparts rotational movement on the cutting head. It will be apparent that the rotational movement can be imparted either by provision of a suitable motor or by simple hand rotation of the handle or shank.

The device illustrated in FIG. 17 can be adapted to provide an implement which can be used as a means to stimulate angiogenesis. The rotating head has a substantially flat end with a few pins protruding above the surface by around 1 mm or less. This instrument could be used after the removal of cartilage from the defective site as described above. The bone scoring instrument would then be brought into contact with the bone and rotated while being moved under pressure, for a short period during which adequate scoring of the bone can be achieved. An illustration of such a device is shown in FIG. 22.

Preferably the anchoring means comprises a tubular device for pushing the retaining means, in the form of a thin mesh, into the groove. Alternatively, if the groove conformation is polygonal the anchoring means is suitably adapted to facilitate the securing of the retaining means. For example, such anchoring means can be a straight-edged blade.

In a further aspect of the present invention, there is provided a replacement element for the repair of damaged tissue present at or on the surface of bone in an animal, including a human being, said element comprising a pad of bio-compatible material shaped and dimensioned to occupy a site from which the damaged tissue, or a part thereof, has been removed.

It will be apparent to one of skill in the art that a replacement element can comprise tissue (eg cartilage, periosteum, bone, synovium) or synthetic material. Alternatively, the replacement element can be fluid or gel injected into the recess after removal of damaged tissue. It will also be apparent that combinations of natural tissues and synthetic materials may be advantageously utilised to repair damaged regions.

The replacement element or implant may form part of a larger sheet of bio-compatible material which is located on a backing sheet, the element being defined in the sheet and being readily removable therefrom. Preferably the larger sheet includes a covering layer.

In a further aspect, the present invention provides a replacement kit for the repair of damaged tissue present at or on the surface of bone in an animal, the kit comprising at least one replacement element of the invention and means anchorable to the bone so as to retain the replacement element at a site from which damaged tissue has been removed, said retaining means being capable of anchoring location within a groove formed in the bone about said site.

The replacement kit may include the set of instruments of the invention as well as at least one replacement element and the retaining means.

A BRIEF DESCRIPTION OF THE DRAWINGS

The accompanying drawings are as follows:

FIG. 1 illustrates cartilage repair by a method of the present invention;

FIG. 2 shows a reamer which is one of the instruments used in the present invention;

FIG. 3 illustrates the operative site after use of the reamer of FIG. 2;

DETAILED DESCRIPTION OF THE INVENTION

Figure 4:
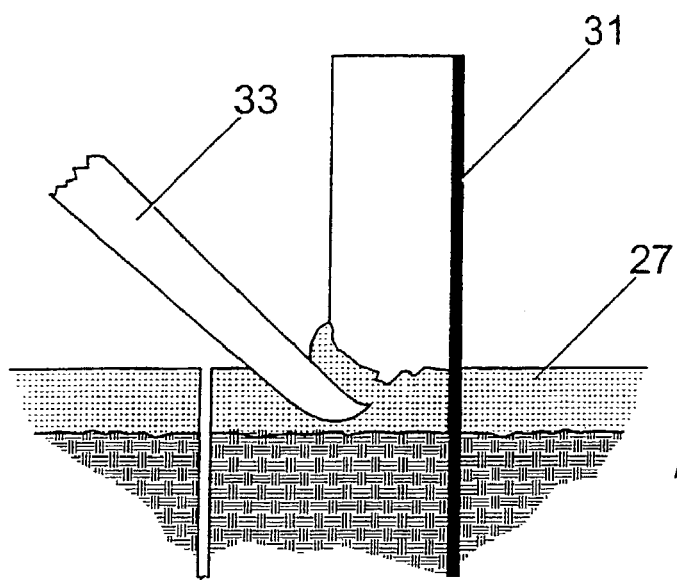
FIG. 4 illustrates in section the use of a scraper forming one of a set of instruments of the present invention.

The invention will now be further described, with reference to the accompanying drawings, and by way of examples only.

Referring to FIG. 1 of the accompanying drawings, there is illustrated part of a knee joint 1 including bone 3 overlaid with cartilage 5. The method of the present invention involves the formation of an annular space or groove 7 which extends through the cartilage and into the bone terminating within the bone at a level that is a multiple of cartilage depth, for example, four or five times the depth of the cartilage.

Removal of the damaged cartilage from the area of bone defined by the groove 7 results in a space into which is located a small piece or pad of biocompatible material 9. Pad 9 is shaped and dimensioned to occupy substantially the whole of the space previously occupied by cartilage and the depth of pad 9 corresponds approximately to that of the surrounding cartilage 5.

Figure 12:
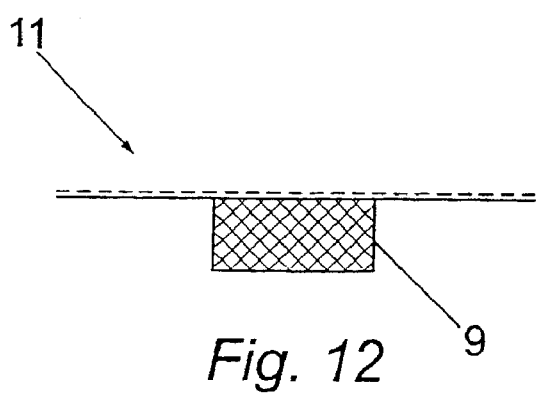
FIG. 12 illustrates an integral pad/retaining means.

FIG. 12 shows an alternative pad arrangement. In this example the pad and retaining sheet form an integral unit which facilitates application to an area to be repaired.

Figure 14:
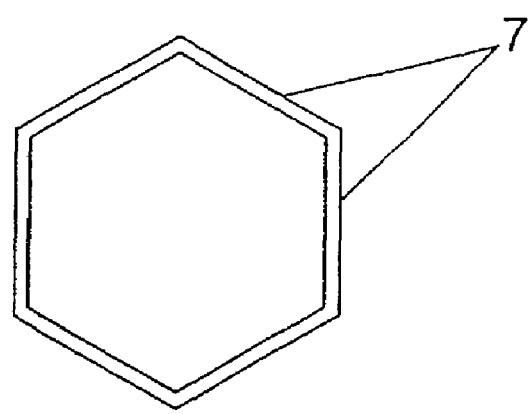
FIG. 14 illustrates an alternative groove arrangement.
Figure 15:
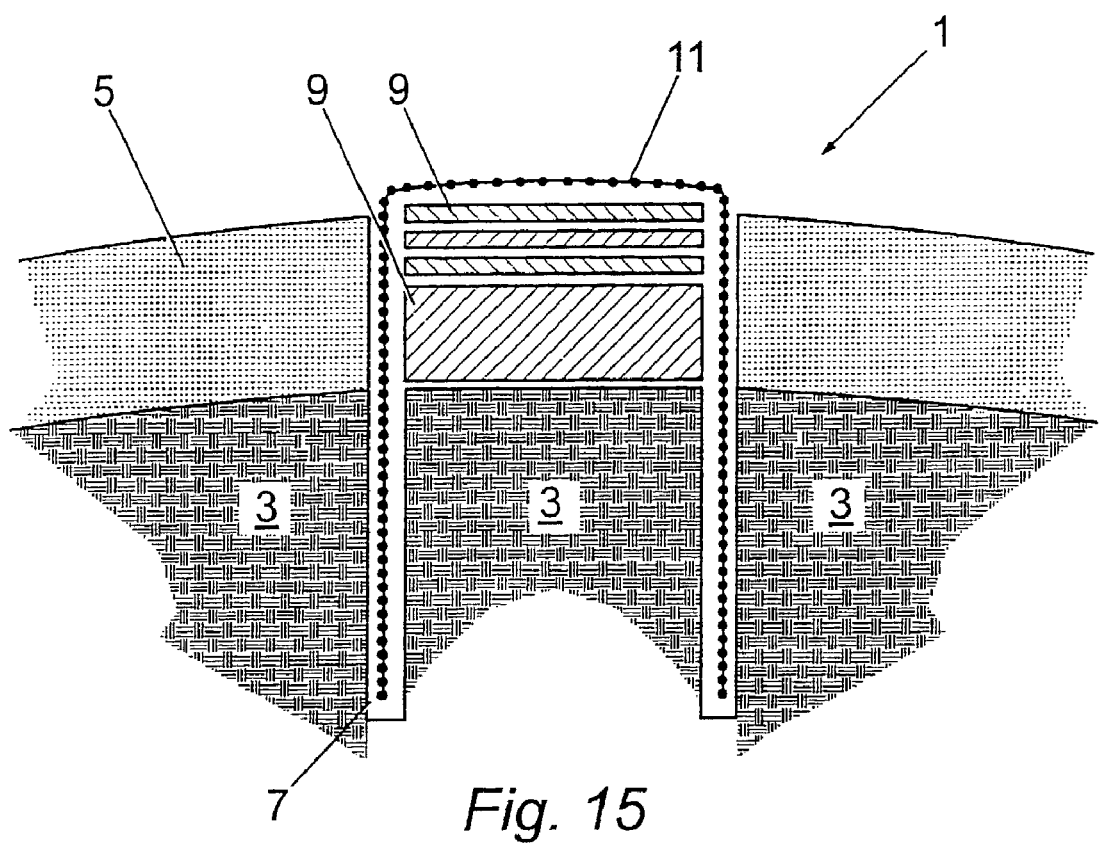
FIG. 15 illustrates a plurality of pads comprising replacement material for use in tissue repair.

The groove illustrated in FIG. 1 is circular in form. Alternative forms are envisaged. For example, FIG. 14 shows a polygonal groove arrangement. It will be apparent that pads of replacement material are adapted to account for differences in groove arrangement.

Pad 9 is made of a non-woven fabric of a bio-enhancing material which is designed to encourage cell recruitment at a level many times that of untreated material.

Pad 9 may also be bio-absorbable at a rate which is designed to match that of the establishment of a new cartilage layer which is secured to the underlying bone and the surrounding cartilage 5.

Gene therapy involves the transfer and stable insertion of new genetic material into cells for the therapeutic treatment. Stem cells or pluripotent progenitor cells are suitable targets for gene transfer because the various progeny lineages produced by these cells will potentially express the foreign gene.

Some studies in gene therapy have focused on the use of haematopoietic stem cells. High efficiency gene transfer systems for hematopoietic progenitor cell transformation have been investigated for use (Morrow, J F, 1976, Ann, NY Acad. Sci 265:13; Salzar, W et al, 1981 in Organization and Expression of Globin Genes, AR Liss, Inc, New York, p313; Bernstein A 1985 in Genetic Engineering: Principles and Methods, Plenum Press, New York, p 235; Dick J E et al 1986, Trends in Genetics 2:165). Viral vector systems indicate a higher efficiency of transformation than DNA-mediated gene transfer procedures (eg $CaPO_4$ precipitation and DEAE dextran) and show the capability of integrating transferred genes stably in a wide variety of cell types. Recombinant retrovirus vectors have been widely used experimentally to transduce hematopoietic stem and progenitor cells.

Methods of gene transfer include microinjection, electroporation, liposomes, chromosome transfer, and transfection techniques (Cline M J 1985, supra). Salser et al used a calcium-precipitation transfection technique to transfer a methotrexate-resistant dihydrofolate reductase (DHFR) or the herpes simplex virus thymidine kinase gene, and a human globin gene into murine hematopoietic stem cells. In vivo expression of the DHFR and thymidine kinase genes in stem cell progeny was demonstrated (Salser W et al, 1981 in Organization and Expression of Globin Genes, Alan R Liss, Inc, New York, pp 313-334).

As an alternative, the prosthetic material 9 may be seeded naturally with cells from the joint after the operation.

It may be a useful step in the cartilage repair procedure described, to seed the non-woven pad with autologous cells from the patient, for example, chondrocytes, fibroblasts, stem cell progenitor cells of chondrocytes or fibroblasts. The source of these would be the residual cartilage at the defect site which is removed with the rotatory instrument. A fraction of the cartilage residue will be healthy cartilage. On removal of this residue, it is proposed to decimate it further with tissue disrupting devices which are known in the art or any mechanical or chemical means which can effectively release healthy chondrocytes, fibroblasts or stem cells. A non-limiting example of such a device would be a dounce homogeniser.

With the addition of the appropriate medium to the decimated cartilage removed from the repair site, the result would be a cell suspension into which the repair pad can be soaked for a period after which the pad is implanted according to the invention. The tissue disrupting device can be used with alternative tissue such as synovium harvested from the patient and used in the same manner, except that in this case the cells seeding the pad would be synovial fibroblasts instead of chondrocytes. The advantage of the above is that autologous cells would be used and therefore not rejected by the patient. The use of the pad ensures that much of the cells remain in the site of repair. It is envisaged that the cells would proliferate resulting in inducing tissue that fills the pad in a faster manner than if the latter was not seeded.

Once the material 9 has been positioned at the site from which the damaged tissue has been removed, a piece of thin netting/mesh or tissue 11 is then located in the position illustrated in FIG. 1. Mesh 11 extends over the pad 9 and into the annular groove 7 into which it is a push-fit. Thus element 11 is a mesh also made of a bio-absorbable material, again calculated to be eliminated at a rate compatible with the growth and fixation of the new cartilage to both the bone and the surrounding cartilage. Element 11 may also be non-woven fabric of a bio-enhancing material, or alternatively can be a piece of tissue, (eg periosteum, synovium, fascia, retinaculum).

If cartilage is to be repaired, pad 9 may be supplied in the form of a larger sheet of the same material into which various sizes and shapes of cut-outs have been formed by means of a laser cutting or another suitable means (eg stamp, water jet). The shapes chosen are those that are easy to generate or cut using standard instruments. A small cartilage defect is best repaired using a circular reamer with a thin wall having cutting teeth. For an irregular shape, it is preferred to use a plurality of prosthetic elements, each being of a simple shape such as a circle, a crescent or a segment of a circle. These are closely packed to cover the entire repair area.

Figure 10:
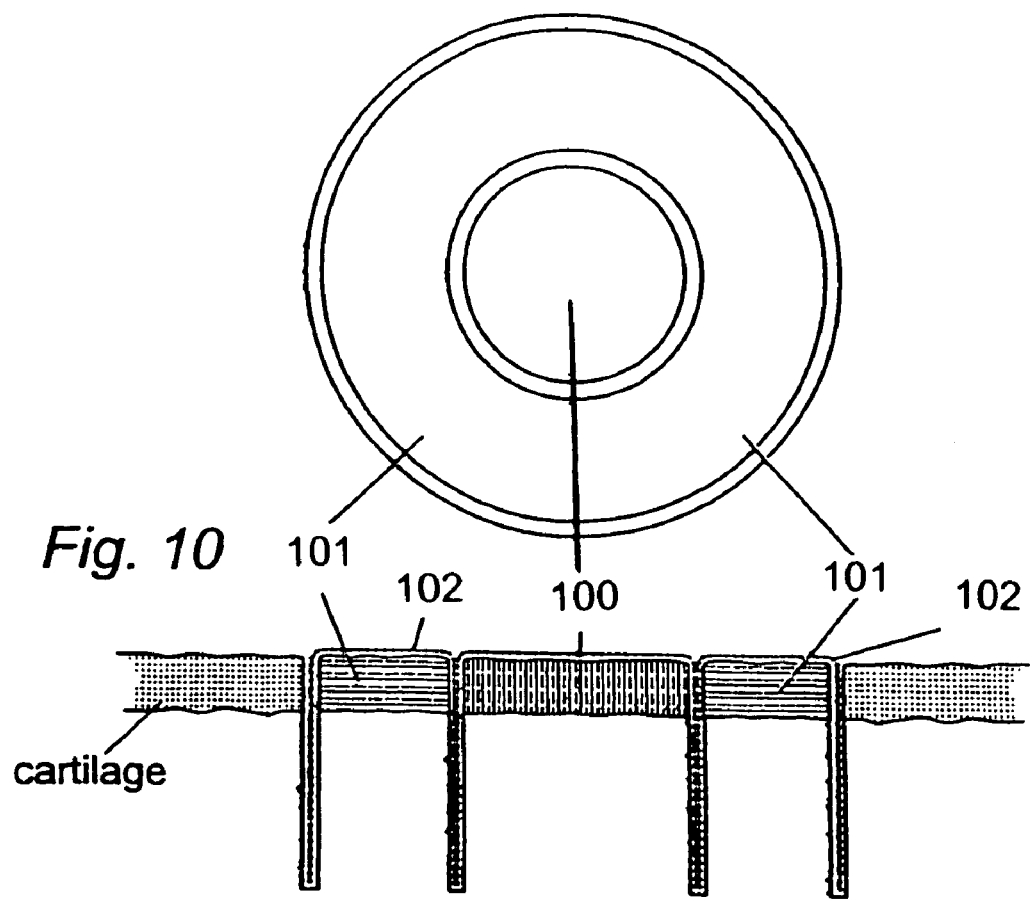
FIG. 10 illustrates cartilage repair of a larger damaged region.

In an alternative arrangement, repair is effected at a damaged area by the use of at least two concentrically reamed grooves, as illustrated in FIG. 10. This requires the use of two replacement elements and at least one retaining sheet. A circular pad of replacement material 100 is applied to the inner concentric circle and a ring-shaped pad 101 is applied to the outer concentric circle. Once in place, each of the pads is secured with at least one retaining sheet 102.

As indicated above, the prosthetic material may form part of a larger sheet which includes a covering or capping layer. The material itself is in the form of a thin layer of a non-woven fabric of a suitable scaffold material which has sufficient strength to be pushed into the circular space previously occupied by the damaged tissue. Typically the material is made of randomly arranged fibres. In the above described embodiment the material is a bio-absorbable material. However in another embodiment the material may be a non-degradable material which is bio-compatible and possesses enhanced surface properties so as to attract tissue growth into the material.

The prosthetic pads themselves can be provided in the form of discs of varying thickness so that the prosthetic scaffold chosen may be of a matching thickness to the adjacent cartilage. As indicated above, it may be supplied in marquetry form with the elements being peeled off when required from a suitable substrate which may be made of, for instance, card. Accordingly the surgeon can select the appropriate elements, including first and subsequent elements, to fill an irregular defect.

The material of the prosthetic elements is the same as that of the covering sheet. The structure is loopy, or random, and stabilised with a bio-compatible adhesive at the sites where the filaments of the material cross or by the entanglement of the filaments.

Referring to FIG. 2 of the accompanying drawings, the operative procedure involves the use of a reamer 15 which is in the form of a circular cross-section tube having a toothed edge 17 at one end. The reamer 15 is provided with a thin steel rod (eg Kirschner wire) 19 having located near one end a cylinder 21 of external diameter such that it is a snug fit within reamer 15. Adjacent cylinder 21, steel rod 19 has a pointed end 23 enabling rod 19, and its associated cylinder 21, to act as a guide for the reamer 15. In use, the pointed end 23 steel rod 19 is located at the centre of the site which includes the damaged cartilage tissue. Light pressure is applied to the steel rod. Reamer 15, located around steel rod 19 and cylinder 21, while being rotated with, for example a power drill, is then subjected to relatively heavy pressure to cut an annular groove which extends through the cartilage and into the bone, as indicated in FIG. 1.

Figure 11:
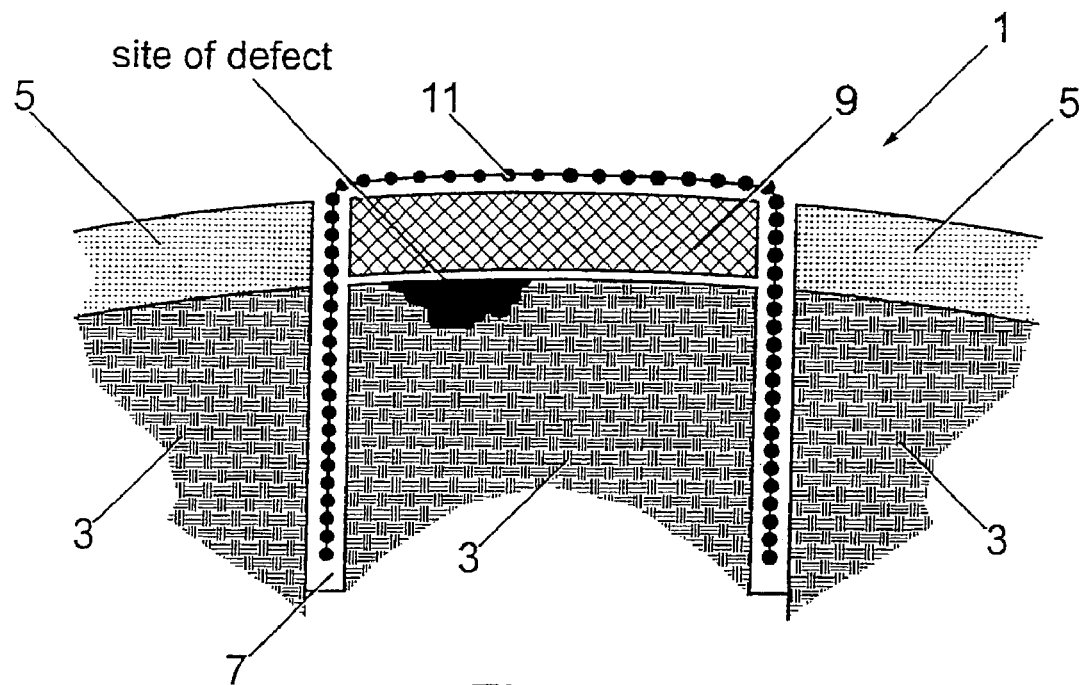
FIG. 11 illustrates the combined repair of both cartilage and bone tissue.

FIG. 3 of the accompanying drawings shows the position after use of reamer 15. An annular groove 25 extends through cartilage 27 and into bone 29 to a depth that is a multiple of the cartilage thickness. In this case the annular groove 25 encompasses the defect site and the surrounding cartilage is healthy. FIG. 11 illustrates an instance where both cartilage and bone tissue is repaired. Prior to application of the pad, replacement material is added to damaged bone. Repair of bone tissue can be with bone,(solid or pulverised), coral, or synthetic bone material.

Figure 5:
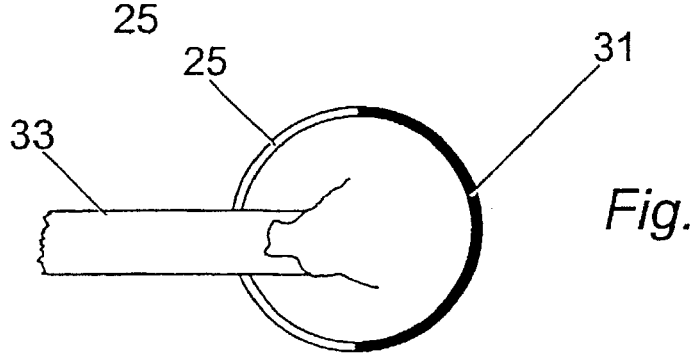
FIG. 5 is a plan view of part of the operative site shown in FIG. 4.

Referring to FIGS. 4 and 5 of the accompanying drawings, there is illustrated removal of cartilage from the area defined by groove 25. In order to effect this cartilage removal, a metallic guard 31 of part-circular cross section is introduced into the groove 25 so as to protect surrounding healthy cartilage 27. A scraper device 33 is then used to effect the removal of the cartilage by causing this tool to penetrate through the cartilage layer and then moving it in a direction towards guard 31.

Figure 9:
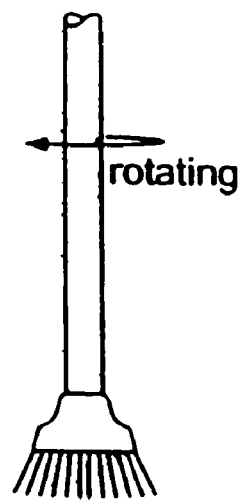
FIG. 9 illustrates a side view of a wire brush device and guide means for removal of damaged tissue.

As stated above, damaged tissue can be removed through the abrasive use of a wire brush as depicted in FIG. 9. The use of a wire brush as an alternative to the scraping device shown in FIGS. 4 and 5 is advantageous since it is less likely to damage the underlying bone. The brush is provided with a guide means which restricts the movement of the brush to the region of damaged tissue thereby preventing unintentional damage to surrounding healthy tissue.

Figure 17:
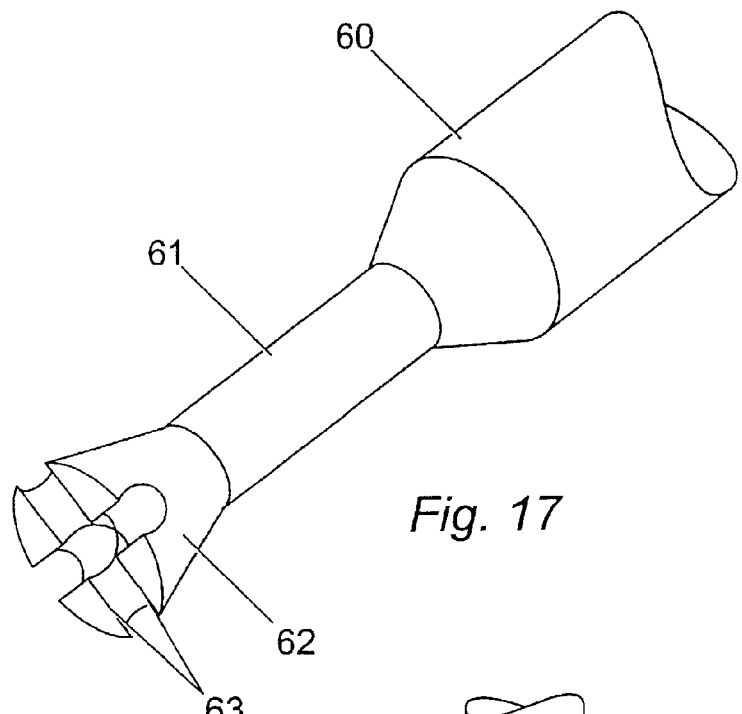
FIG. 17 illustrates an alternative implement for removal of damaged tissue which comprises a handle, shank and cutting head which includes a plurality of cutting edges.
Figure 18:
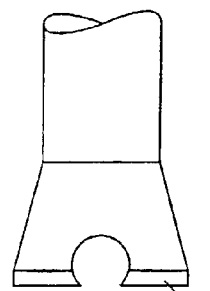
FIG. 18 illustrates a side view of the cutting head.
Figure 19:
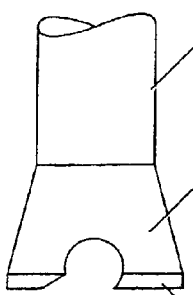
FIG. 19 illustrates a further side view of the cutting head
Figure 20:
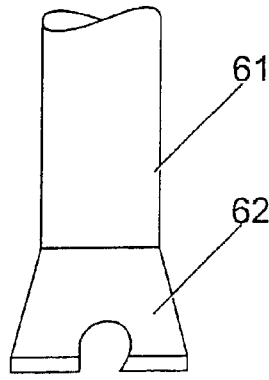
FIG. 20 illustrates a yet further side view of the cutting head.

The implement shown in FIG. 17 is a yet farther device which can be used to remove damaged tissue. FIG. 17 shows an implement comprising a handle 60 which extends into a shank 61 to which is rotatably mounted a cutting head 62 comprising a plurality of cutting edges 63. Alternatively the cutting head can be rotatably mounted on the handle.

In use the cutting action is achieved by rotating the shank while the head is moved over cartilage surface and while applying pressure onto the cutting head. The head has a substantially flat end with sharp edged grooves that are formed by making holes in the head in a perpendicular direction to the axis of rotation and by machining of an appropriate amount of material from the end.

Figure 21:
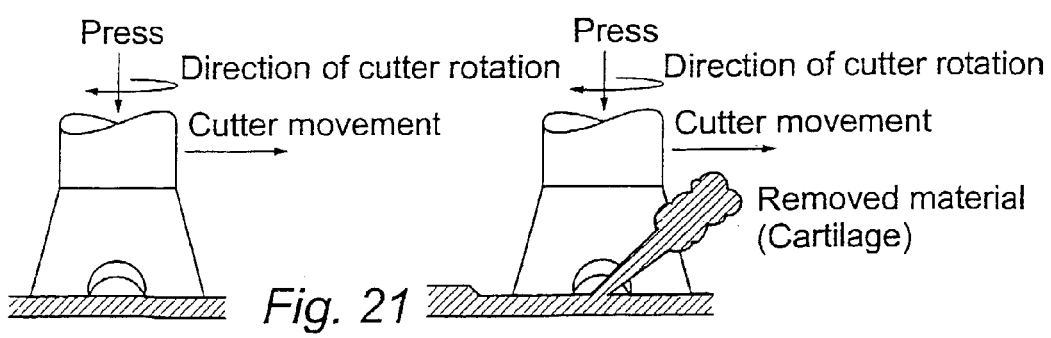
FIG. 21 illustrates the removal of cartilage using the implement shown in FIG. 17.

This instrument is particularly suitable for cutting into a soft material such as cartilage particularly when removing it from the underlying bone causing minimal or no damage to the latter. Referring to FIG. 21, as the instrument is pressed against cartilage, the latter being soft, bulges within the groove and is then subject to the cutting action of the sharp edge of the groove. The material removed escapes side-wards through the groove, as illustrated in FIG. 21. The end of the instrument being flat thus skids over the hard and relatively un-deformable surface of the underlying bone (without damaging it), when the instrument reaches the bony surface, after it has removed the cartilage layer.

In cases of a single repair site, it would be preferable to use a short reamer, which, on completing the groove can be left in situ to act as a guard for the brush during removal of cartilage from the defect site.

Figure 6:
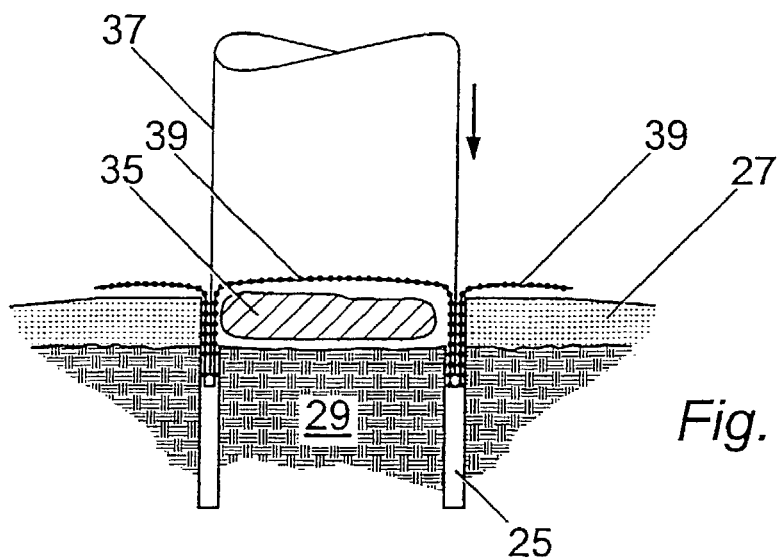
FIG. 6 shows the use of a tubular pusher which is another of the set of instruments of the present invention.

Referring to FIG. 6 of the accompanying drawings, once the damaged cartilage has been removed, a prosthetic pad 35, of a shape appropriate to fill the space previously occupied by the damaged cartilage, is located in that space. A further instrument in the form of a tubular pusher 37 is then used to anchor the prosthetic pad to the bone 29. Tubular pusher 37 has a wall thickness sufficiently thin to enable it to be pushed into groove 25. Before this is effected, a circular sheet of fabric netting 39 (made of non-woven fabric) of a diameter of several times that of pad 35, is laid over the pad so that it extends also over the surrounding healthy cartilage. Pusher 37 is then introduced into groove 25 carrying with it the outer part of netting 39. Pusher 37 is moved farther into groove 25 until the outer edge of netting 39 is pushed fully into groove 25. The pusher 37 is then removed leaving the netting 39 jammed into groove 25. The netting 39 will maintain the pad 35 in place until such time as the pad, whether formed of prosthetic material or ultimately of new cartilage, is itself secured both to the underlying bone 29 and to the surrounding healthy cartilage 27. The covering sheet fabric may have holes to allow bone and tissue to grow throughout, within the groove thus securing the covering sheet further.

Figure 13:
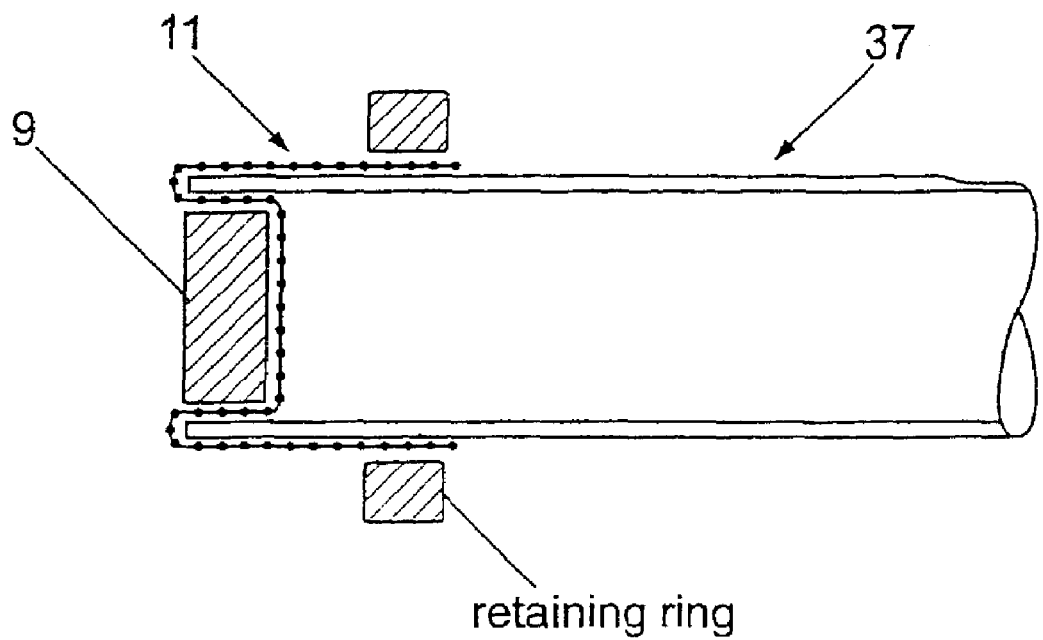
FIG. 13 illustrates an implement used in the application of a pad and retaining means to a region to be repaired.

FIG. 13 shows an alternative use of the pusher 37. In this embodiment the pusher 37 is loaded with a pad and retaining sheet prior to application to the groove. This is particularly suited to the intergral pad/retaining sheet of FIG. 12 and advantageously expedites the application and retention of the pad to a site of repair. The retaining sheet is held in position with a ring that can slide along the pusher as this is used to implant the pad in the repair site and introducing the retaining sheet in the annular groove. Thus, by loading the pusher with the implant and retaining sheet it can be supplied to the surgeon in a sterile package, which, on being opened by the surgeon, can be readily used with no need for any further handling by the surgeon. Further, this particular method of packaging would make facilitate implanting the device through small incisions such as those made in arthroscopic or arthroscopically assisted procedures.

The method of the present invention can be applied in connection with a cartilage defect that is confined to an area less than that of a single circular pad. If the defect is large and/or irregular, it can be dealt with by means of a plurality of pads in the shape of circles, ellipses, crescents or other simple shapes. When securing non-circular pads in position, a pusher can be used that, in section, is part circular, for instance, half circular, quarter circular, etc.

Figures 7A, 7B, 7C:
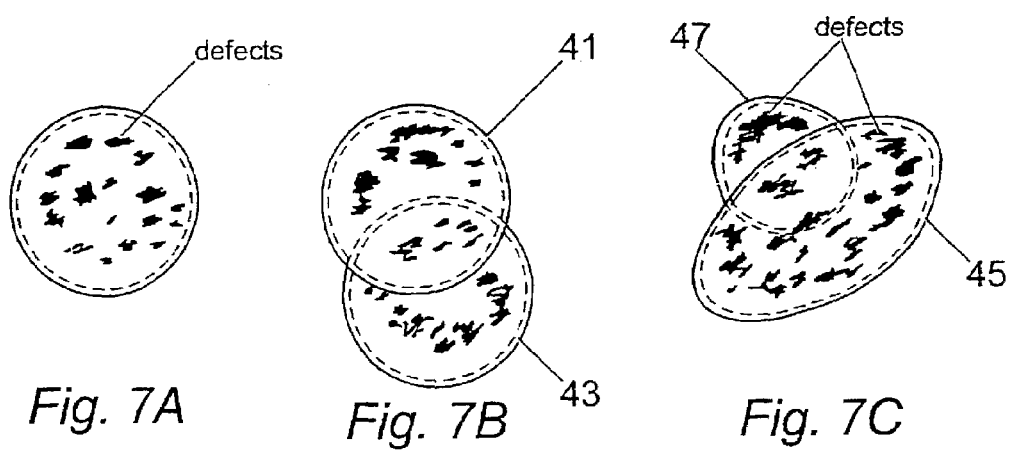
FIG. 7 illustrates repair of various sizes and shapes of damaged cartilage.

FIG. 7 illustrates the use of a single pad which has an, area greater than the whole of the defect area (FIG. 7A). FIG. 7B illustrates the use of a circular pad 41 and an adjacent crescent-shaped pad 43. FIG. 7C illustrates the use of an-elliptical pad 45 as well as a crescent-shaped pad 47. In practice, the surgeon will choose whichever combination of pads most effectively covers the defect area.

It is feasible accordingly to resurface a substantial area of a knee bone if required.

Figure 8:
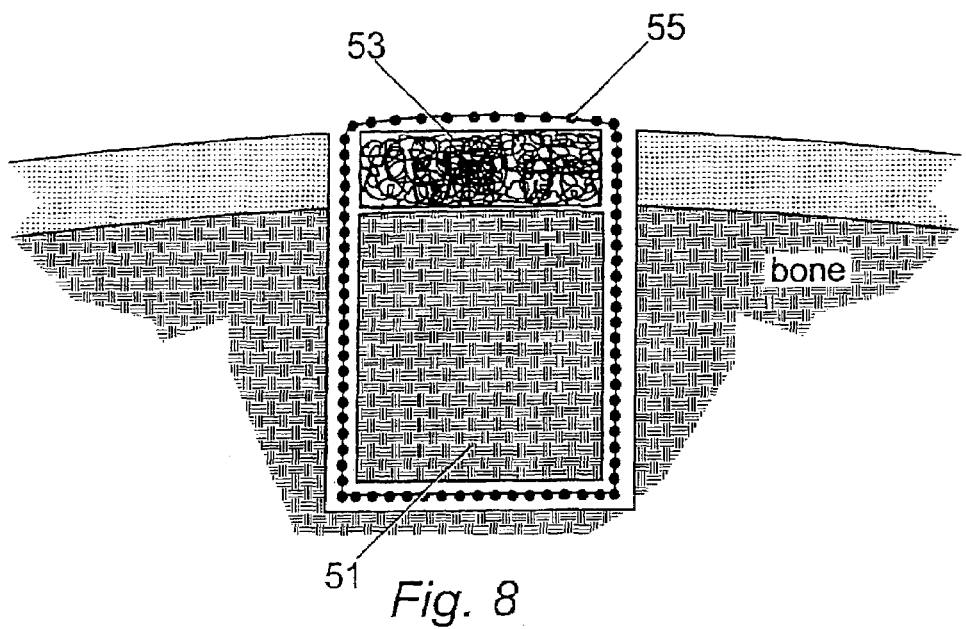
FIG. 8 illustrates cartilage repair using another embodiment of the present invention.

Referring to FIG. 8 of the accompanying drawing, there is illustrated another embodiment of the present invention. In this case an entire bone plug 51, which includes the damaged cartilage, is removed from the bone. A prosthetic pad 53, (to which apply the same attributes of pad 9 previously described), is located on the bone plug in place of the damaged cartilage and an open weave retaining mesh 55 is located around the entire bone plug and pad, thereby securing the pad 53 to the bone plug 51. The bone plug is then repositioned within the bone as shown in FIG. 8. The annular space created between the bone plug and the remaining bone is then occupied by the retaining mesh 55. The bone plug and the host bone will unite through the mesh 55.

Figure 16:
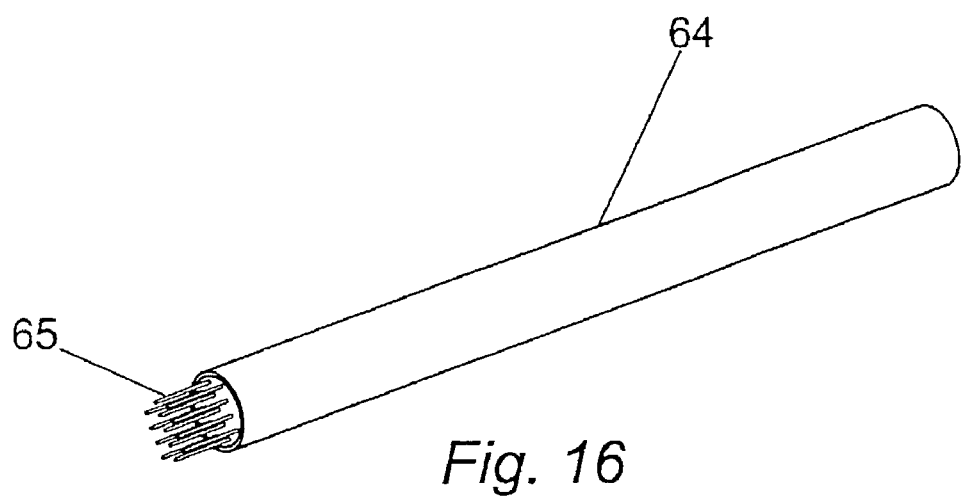
FIG. 16 illustrates an implement from piercing the subchondral bone plate to stimulate angiogenesis.
Figure 22:
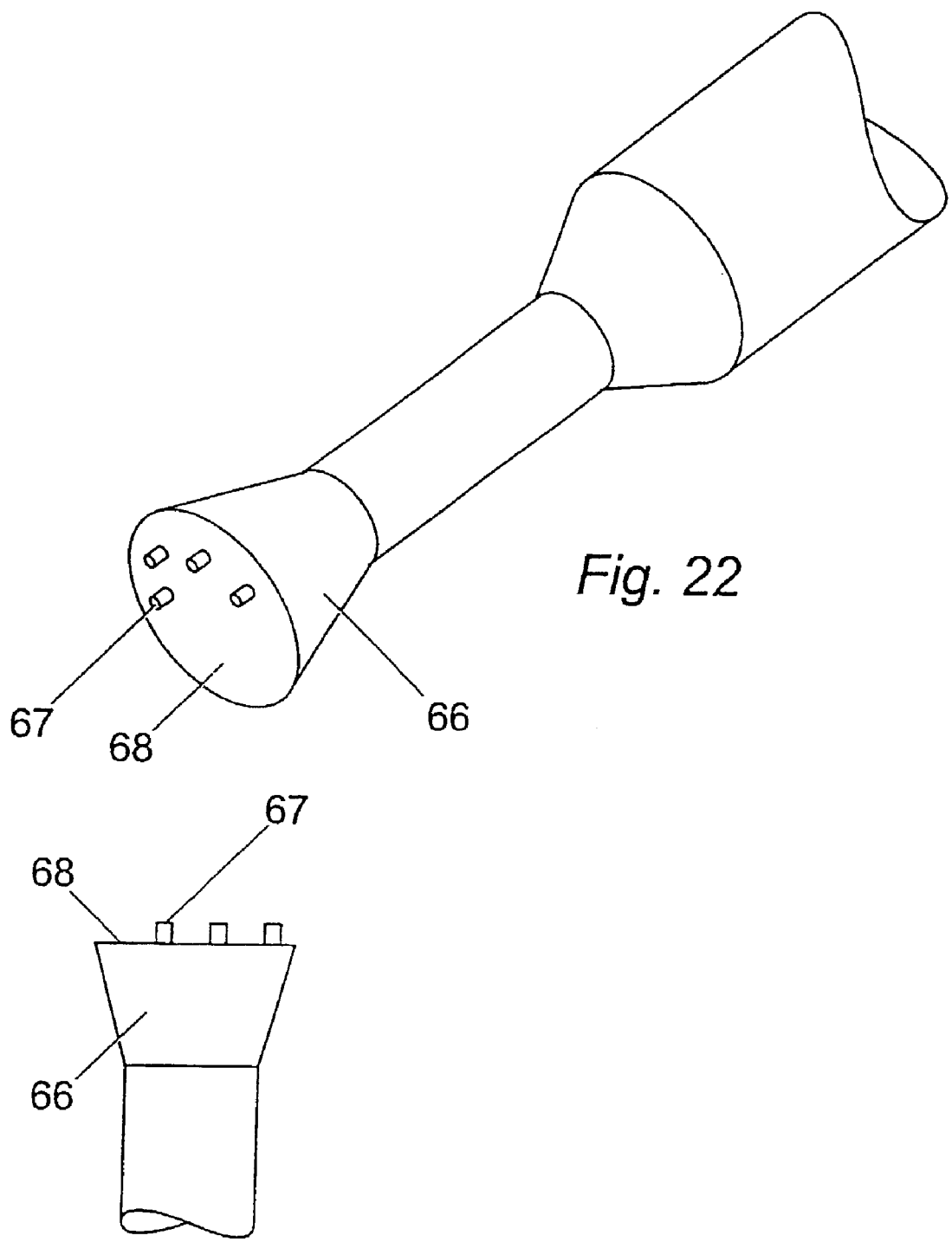
FIG. 22 illustrates an implement for stimulating angiogenesis at a site to be repaired.

Refering to FIGS. 16 and 22, devices are illustrated which can be used to stimulate angiogenesis at a site of repair. FIG. 16 shows a cylindrical rod 64 which is provided with a plurality of needles 65 which can be used to pierce the subchondral plate to promote angiogenesis. FIG. 22 shows a device similar in structure to the device in FIG. 17 but with the cutting head replaced with a rotating head 66 which is provided at least one projection 67 fixed to a substantially flat surface 68. Typically, the projections are approximately 1 mm in height. The application of the rotating head 66 to a tissue surface which has been cleaned of damaged tissue produces an abrasive effect on the bone to score the surface thereby stimulating angiogenesis.

It will be apparent to one skilled in the art that the removable nature of the rotable heads 62 and 66 is advantageous in so far as replacement heads can be easily and quickly exchanged. The handle 60 or shank 61 can be adapted such that new, unused heads can be fixed to the upper portion of the implement thereby providing a compact storage for the heads which also protects the heads from physical damage.

The invention claimed is:

1. A method for the repair of damaged tissue present at or on the surface of bone in an animal, including a human being, the method comprising:
   forming a narrow groove around at least part of said damaged tissue using a cutting device having a toothed cutting edge;
   the groove extending below the damaged tissue into the bone to a depth that is a multiple of the thickness of the damaged tissue;
   removing the damaged tissue within the region defined by the groove to form a cavity in the tissue present on the surface of the bone, the narrow groove extending from the cavity into the bone;
   protecting healthy tissue surrounding the region of the groove during the step of removing damaged tissue using guard means;
   inserting a bio-compatible non-woven pad in the cavity from where the damaged tissue has been removed, the pad configured to encourage cell in-growth at the repair site;
   retaining the pad in the cavity using a thin netting/mesh sheet material extending from the pad and into the groove;
   anchoring the sheet material and the pad in position by pushing the sheet material into the groove to a depth into the bone underlying the cavity from which the damaged tissue has been removed using a pusher tool; and
   removing the pusher tool from the groove to leave the sheet material jammed into the groove.

2. A method according to claim 1, wherein said method is a method of replacing or repairing tissues associated with bone tissue.

3. A method according claim 1, wherein the depth of the groove is at least four times that of the thickness of tissue which is replaced.

4. A method according to claim 1, wherein the replacement material is in the form of a circular, crescent-shaped, ring-shaped or part circular pad.

5. A method according to claim 1, wherein the replacement material is bio-absorbable and bioenhanced.

6. A method according to claim 1, wherein the replacement material is non-bioabsorbable and bioenhanced.

7. A method according to claim 1, wherein the replacement material is seeded with cells that are: chondrocytes; fibroblasts; mesenchymal progenitor cells; endosteal cells; periosteal cells; or inducible chondroprogenitor cells from extraskeletal organs.

8. A method according to claim 7, wherein said replacement material is seeded with chondrocytes.

9. A method according to claim 7, wherein the cells are derived from tissue material removed from the site to be repaired.

10. A method according to claim 7, wherein said seeded cells are genetically engineered.

11. The method according to claim 1, wherein the narrow groove is formed using a reaming device comprising a tube having a cutting edge at one end and a rod displaced within the tube having located adjacent one end a cylinder wherein, adjacent to the cylinder, the rod is provided with a point that, when applied at the surface of the damaged bone tissue to be repaired, acts as a guide for the reaming device.

12. The method according to claim 1, wherein removing at least part of the damaged tissue comprises removing the damaged tissue using a scraping device.

13. The method according to claim 1, wherein guard means is at least part circular for location in the groove.

14. The method according to claim 1, wherein removing at least part of the damaged tissue comprises removing the damaged tissue using a wire brush.

15. The method according to claim 14, wherein the wire brush is provided with guide means.

16. The method according to claim 1, wherein the pusher tool comprises a tubular device for pushing the retainer into the groove.

17. The method according to claim 16, wherein the tubular device is preloaded with the sheet material and the bio-compatible pad.

18. The method according to claim 16, wherein the tubular device further comprises a retaining ring slidably mounted about the tubular device to secure the retainer and facilitate the application of the bio-compatible pad.

19. The method according to claim 1, wherein removing at least part of the damaged tissue comprises removing the damaged tissue using a cutting head rotatably mounted upon a support member.

20. The method according to claim 19, wherein the cutting head is provided with at least one projection.

21. The method according to claim 1, wherein the pad is shaped and dimensioned to occupy a site from which the damaged tissue, or part thereof, has been removed.

22. The method according to claim 21, wherein the pad and the sheet material are integral.

23. The method according to claim 1, wherein the bio-compatible pad is cartilage, periosteum, bone, or synovium.

24. The method according to claim 1, wherein the bio-compatible pad is a synthetic bio-compatible sheet.

* * * * *